(12) United States Patent
Katsnelson et al.

(10) Patent No.: US 11,491,330 B2
(45) Date of Patent: Nov. 8, 2022

(54) WELLNESS DEVICE USING INTERFERENCE FREQUENCIES

(71) Applicants: Yakov Katsnelson, Edgewater, NJ (US); Vladimir Chuev, Moscow (RU); Hank Beckhoff, Doylestown, PA (US)

(72) Inventors: Yakov Katsnelson, Edgewater, NJ (US); Vladimir Chuev, Moscow (RU); Hank Beckhoff, Doylestown, PA (US)

(73) Assignee: HEBY, LLC, Dover, DE (US)

( * ) Notice: Subject to any disclaimer, the term of this patent is extended or adjusted under 35 U.S.C. 154(b) by 0 days.

(21) Appl. No.: 17/564,294

(22) Filed: Dec. 29, 2021

(65) Prior Publication Data
US 2022/0226650 A1 Jul. 21, 2022

Related U.S. Application Data

(60) Provisional application No. 63/139,580, filed on Jan. 20, 2021.

(51) Int. Cl.
*A61N 1/36* (2006.01)
*A61N 1/32* (2006.01)
*A61N 1/04* (2006.01)

(52) U.S. Cl.
CPC ....... *A61N 1/36021* (2013.01); *A61N 1/0456* (2013.01); *A61N 1/0492* (2013.01); *A61N 1/323* (2013.01); *A61N 1/36034* (2017.08)

(58) Field of Classification Search
CPC ............. A61N 1/36021; A61N 1/0456; A61N 1/0492; A61N 1/323; A61N 1/36034
See application file for complete search history.

(56) References Cited

U.S. PATENT DOCUMENTS

| | | | |
|---|---|---|---|
| 4,023,574 A | 5/1977 | Nemec | |
| 4,848,347 A | 7/1989 | Hall | |
| 5,476,481 A | 12/1995 | Schondorf | |
| 5,817,138 A | 10/1998 | Suzuki | |
| 7,949,403 B2 | 5/2011 | Palermo et al. | |
| 9,802,039 B2 | 10/2017 | Palermo et al. | |
| 10,279,174 B2 | 5/2019 | Southwell et al. | |
| 2005/0277997 A1 | 12/2005 | Ohta et al. | |
| 2007/0142874 A1* | 6/2007 | John | A61N 2/006 607/45 |
| 2007/0299895 A1* | 12/2007 | Johnson | G06F 1/0321 708/270 |
| 2008/0208287 A1 | 8/2008 | Palermo et al. | |
| 2014/0330345 A1 | 11/2014 | John | |
| 2017/0218594 A1 | 8/2017 | Padilla | |
| 2018/0117317 A1 | 5/2018 | Oku et al. | |
| 2019/0083783 A1 | 3/2019 | Southwell et al. | |

FOREIGN PATENT DOCUMENTS

| | | |
|---|---|---|
| DE | 2159437 B1 | 4/1973 |
| WO | 2020161555 A1 | 8/2020 |

OTHER PUBLICATIONS

International Search Report and Written Opinion. PCT/US22/12855, dated Apr. 1, 2022. 13 pages.

\* cited by examiner

*Primary Examiner* — Amanda K Hulbert
*Assistant Examiner* — Philip C Edwards
(74) *Attorney, Agent, or Firm* — Gearhart Law LLC

(57) ABSTRACT

A wellness device is provided that utilizes interference frequencies. The wellness device applies frequencies modulated by one another to interfere with one another to create a unique frequency delivery to achieve a desired result.

16 Claims, 4 Drawing Sheets

WELLNESS DEVICE USING INTERFERENCE FREQUENCIES

CLAIM OF PRIORITY

This application claims priority to U.S. Application 63/139,580 which was filed on Jan. 20, 2021, the contents of which are herein fully incorporated by reference in its entirety.

FIELD OF THE EMBODIMENTS

The field of the present invention and its embodiments relate to a wellness device for the noninvasive application of electrical pulses to a user. In particular, the wellness device utilizes interference frequencies to achieve the desired result.

BACKGROUND OF THE EMBODIMENTS

The present application relates generally to the treatment of the human body and, more particularly, to an apparatus that utilizes electrical current(s) to treat one or more patients. Generally, it is known in the art to treat a patient experiencing pain or other symptoms related to depression, anxiety, and/or other psycho-emotional disturbances (including general well-being condition) using electrostimulation of deep brain structures. However, the method and manner in which that electrostimulation is delivered is key to success with the patient as well as minimizing deleterious side effects.

Electrostimulation treatments bring about a therapeutic benefit by stimulating the brain, nerves, and muscles of the patient to rehabilitate injuries to the nerves or muscles and to relieve pain, depression, anxiety, or other psycho-emotional disturbances, including general well-being conditions.

In interference current therapy, two (or more) currents that are independent of each other are applied by means of electrodes placed on the skin. These currents, which may respectively be ineffective for stimulation, present frequencies that differ by a low-frequency difference. These currents penetrate the depth of the area of treatment so as to interfere with each other and thereby produce a low-frequency beat that corresponds to the frequency difference. This low beat frequency, because of the physiological properties of the nerve and brain structures, is stimulating.

Review of Related Technology:

U.S. Pat. No. 10,279,174 pertains to a device for transcutaneous electrical stimulation. The device comprises circuitry configured to generate transcutaneous stimulation signals. The device also comprises a first signal output component for electrically connecting to a first electrode connector to deliver generated transcutaneous stimulation signals. The first signal output component comprises a first four-pole electrical connector part. The device further comprises a second signal output component for electrically connecting to a second electrode connector to deliver generated transcutaneous stimulation signals. The second signal output component comprises a second four-pole electrical connector part. The device further comprises a controller to selectively control the output of the stimulation signals to selected pairs of poles across the first and second four-pole electrical connector parts. Each selected pair of poles comprises one pole from the first four-pole electrical connector part and one pole from the second four-pole electrical connector part.

U.S. Pat. No. 5,817,138 pertains to an interferential wave, microcurrent device. The device typically has a power supply, a frequency generator, a pulse generator, a pulse envelope generator, an electrical current controller, and four or more channels for applying micro amperes of electrical current to patient tissue. Each channel has two electrodes for completing a micro current electrical circuit through patient tissue. The controller provides a controlled amount of current in each channel from about 20 micro amperes to about 200 micro amperes at a frequency up to about 300 Hertz. Also disclosed are methods for treating lymphedema, edema, fibrosis, and fibromyalgia by application of interferential wave form micro current.

U.S. Pat. No. 4,023,574 pertains to a device where three separate pairs of electrodes are attached to a body part to be treated, spaced apart around said part of the body. A primary alternating electrical current having a primary frequency of between 100 Hz and 100,000 Hz is passed between one of the electrode pairs. A similar second alternating electrical current having a secondary frequency in the same range as the primary frequency but differing by between 50 Hz and 100 Hz from the primary frequency is passed between another of the pairs of electrodes. A tertiary alternating current is passed between the third pair of electrodes and has a tertiary frequency differing by at most 1 Hz from the frequency of either the primary current, the secondary current, or the arithmetic means of the frequency of these two currents.

U.S. Patent Application Publication 2019/0083783 pertains to a method of treating a waste evacuation dysfunction, comprising administering transcutaneous electrical stimulation (TES) to at least one lower pelvic and/or sacral region for at least one treatment period per day over a treatment term of at least one week.

Various systems and methodologies are known in the art. However, their structure and means of operation are different from the present disclosure. The other inventions fail to solve all the problems taught by the present disclosure. At least one embodiment of this invention is presented in the drawings below and will be described in more detail herein.

SUMMARY OF THE EMBODIMENTS

The present invention and its embodiments relate to a wellness device configured to provide interference frequencies to a user. Biophysics, clinical and experimental publications contain a wealth of information on the effects of the influence of electric and magnetic fields on the biological processes occurring in a living organism[1]. A special place in this problem is occupied by transcranial electrical stimulation (TES) of the brain, which is a process of influencing the brain with electric fields formed either by contact or non-contact methods in order to affect and influence these biological processes.[2] In the first case, the effect is performed by placing external electrodes (or electrodes implanted under the skin or in brain structures) on the mammal's scalp with alternating electric voltage; as a result, drift current and bias current flow between each pair of electrodes simultaneously.

[1] Wood A., Mate R., Karipidis K., //Meta-analysis of in vitro and in vivo studies of the biological effects of low-level millimetre waves. Journal of Exposure Science and Environmental Epidemiology. 2021. 16 March.—P. 1-8.—doi:10.1038/s41370-021-00307-7; Bingi V. N., Savin A. V. Physical problems of action of weak magnetic fields on biological systems. //UFN. 2003. T. 173. Vol. 3 P 265-300; Bingi P. N. Principles of electromagnetic biophysics. M.: FIZMATLIT, 2011. 592 c. ISBN 978-5-9221-1333-5
[2] Lebedev V. P., Katsnelson Ya. S. //TRANSCRANIAL ELECTRIC STIMULATION: ANALGESIA AND ALLIED EFFECTS. In: Automatization in physiological investigations. Leningrad. "Nauka". 1988, pp. 198-202; Vonti A. O. Ilyinskv. A. V. Katznelson J. S., Shadrin E. B., Effect of extremely high frequency radiation on serotonin production in a living organism. //Letters in ZhTF, 2018. Vol. 44. Iss. 17, C. 27-33

In general, both types of current flow both inside the skull and over the outer skin of the scalp. In the second case, the current action is conducted by placing the brain in a high-frequency electromagnetic field, which causes induction currents to flow in the outer skin of the head due to the high electrical conductivity of the skin, defined by a branched network of microcapillaries. The microcapillaries contain highly conductive blood plasma, cellular elements, and erythrocyte aggregates, which interact through the walls of the vessels interact via transport proteins within the cerebrospinal fluid circulating within the cavities of the Virchow-Robin space around the microcapillaries[3].

[3]Brinker T., Stopa E., Morrison J., Klinge P. A new look at cerebrospinal fluid circulation //CNS 2014. V.11. P.10. DOI: 10.1186/2045-8118-11-10

There is no doubt that in most cases has a beneficial effect on the clinical and psychosomatic state of the body, reducing the intensity of the pain syndrome, reducing the severity of the depressive syndrome, panic attacks, and some other psycho-emotional disorders. However, the procedure of studying the physical causes behind these processes is far from complete, which is why there is a great deal of interest in this kind of research. It is now generally accepted that the production of serotonin and beta-endorphins by the antinociceptive structures of the brain is able to reduce the level of pain syndrome and psychoemotional disorders, leading to a normalization of neurohumoral homeostasis.

The present application presents a more effective modality than known algorithms by using interference currents, for in the activation of serotonergic and beta-endorphinergic structures of the brain. The end result being, in particular, to initiate the normalization of neurohumoral homeostasis. The starting point for the development of the new algorithm was the information that the increased beta-endorphin content in brain structures was maximal when using an earlier version of the TES with a repetition rate of 78 Hz for stimulation pulses.[4]

[4]Airapetov L. N., Zaitchik A. M., Trukhmanov M. S., Lebcdev V. P., Sorokoumov V. A., Katsnelson Ya. S., Abisogomian V. G., Kodzayev Yu. K. *Changes in the beta-endorphin levels in brain and cerebrospinal fluid in transcranial electroanalgesia.* Fiziol. zhurn. SSSR, 1985. 71, 1. 56-64: David A. Gruenewald, Alvin M. Matsumoto. Hypothalamic Changes Relevant to Reproduction in Aging Male Rodents: "Functional Neurobiology of Aging,". 2000, 960 pages.

In at least one embodiment of the present invention there is a method of increasing pain threshold via a wellness device, the method comprising the steps of: applying, to a user, a first set of bipolar pulses having a first frequency; applying, to the user, a second set of bipolar pulses having a second frequency; applying, to the user, a carrier frequency; wherein the first set of bipolar pulses and the second set of bipolar pulses and the carrier frequency are applied to the user via electrodes; and wherein the first set of bipolar pulses and the second set of bipolar pulses create interference at about 9 Hz to about 12 Hz and/or 76 Hz to about 80 Hz.

In yet another embodiment of the present invention there is a method of increasing pain threshold via a wellness device, the method comprising the steps of: applying, to a user, a first set of bipolar pulses having a first frequency, wherein the first frequency is in a range of about 88 Hz to about 96 Hz; applying, to the user, a second set of bipolar pulses having a second frequency, wherein the second frequency is in a range of about 62 Hz to about 68 Hz; applying, to the user, a carrier frequency, wherein the carrier frequency is in a range of about 300 kHz to about 500 kHz, and wherein a polarity of the carrier frequency is periodically inverted; wherein the first set of bipolar pulses and the second set of bipolar pulses and the carrier frequency are applied to the user via electrodes; and wherein the first frequency and the second frequency create interference at about 9 Hz to about 12 Hz and/or 76 Hz to about 80 Hz.

In yet another embodiment of the present invention there is a method of stimulating serotonergic structures, experimentally confirmed by a slowdown in the development of a conditioned reflex via a wellness device, the method comprising the steps of; applying, to a user, a first set of bipolar pulses having a first frequency; applying, to the user, a second of bipolar pulses having a second frequency; applying, to the user, a carrier frequency, wherein the first set of bipolar pulses and the second set of bipolar pulses and the carrier frequency are applied to the user via electrodes.

DESCRIPTION OF THE PREFERRED EMBODIMENTS

Figure 1:
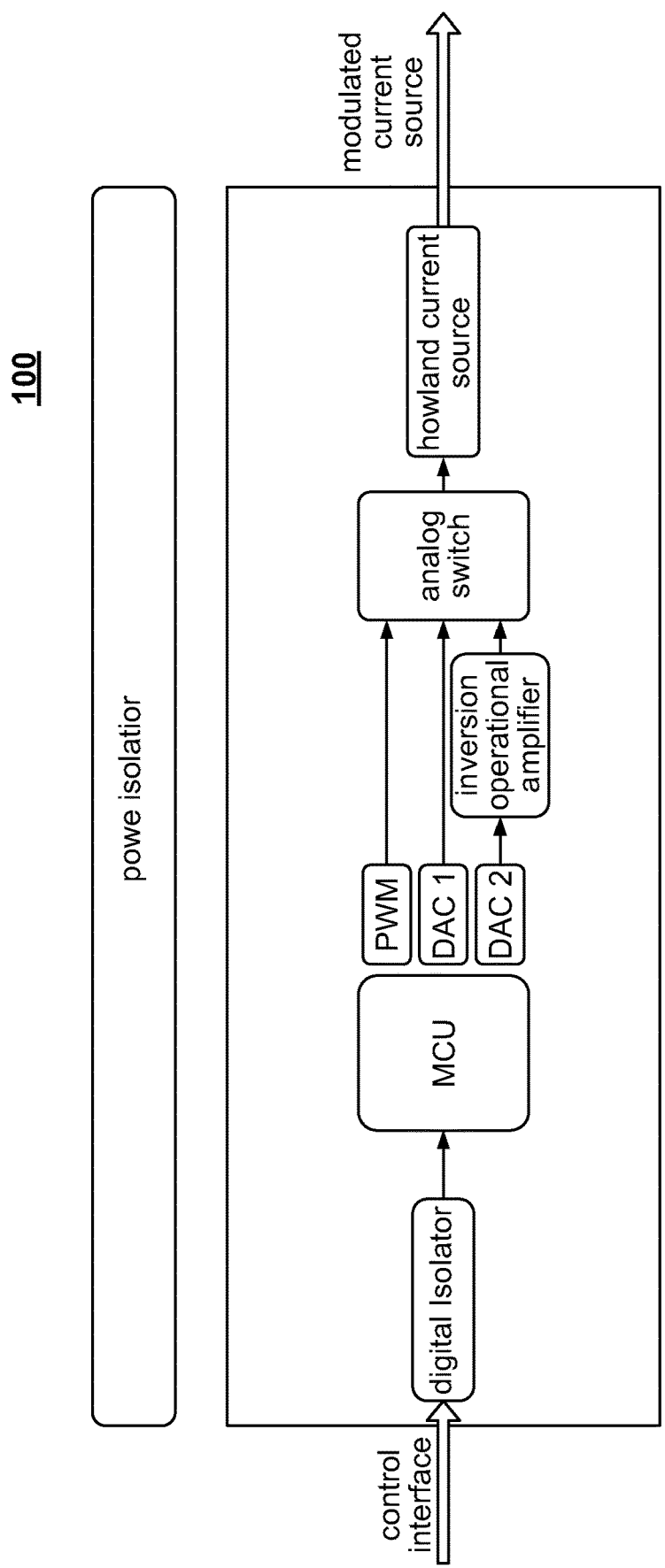
FIG. 1 is a schematic showing an assembly of one embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

For the purposes of this application, "about" is intended to mean the value or values provided as well as a variance of up for −10% to +10% for any given value. For example, about 100 means any number from 90 to 110 and includes 100. Further, whole numbers and fractional numbers (90.2, 90.3, etc.) are included within this definition.

The proposed algorithm employed by the embodiments of the present application is directed to the formation of two or more mutually perpendicular alternating currents in the brain, each interfering with each other in the area where the current tubes intersect. The proposed algorithm is designed to increase the intensity of serotonin and beta-endorphin production in deep brain tissues more effectively than the commonly known methods due to the process of current interference in targeted deep brain structures.

To ensure interference effects, this algorithm uses four (4) or more electrodes in the form of two (2) or more pairs: one pair provides a current tube in the basal front-occipital direction, while the other pair(s) of electrodes are positioned on the mastoidal region and/or other areas of the scalp, forming a second line of current tubes perpendicular to the first. Using two or more pairs of electrodes creates two or more overlapping lines of current tubes in the brain with a controlled crossing zone in which the interference of currents induced in the deep brain tissue occurred.

The length of the high-frequency electromagnetic wave playing the role of a carrier is several meters. This was shown by a simple calculation using literature values of the dielectric permittivity of brain tissue, from which it follows those oscillations of currents in the interference region are summarized, alternately amplifying, or weakening each other in time and covering the entire interference zone spatially uniformly. By using bipolar impulses with two different repetition frequencies, for example, 68 Hz and 88 Hz, to modulate the high-frequency carrier impulses (for example 500 kHz) creates an interference area as there are oscillations occurring at a frequency equal to the half-sum and half—a difference of the modulating frequencies and low-frequency beats. Thus, the interference area is subjected to oscillations with a frequency of 78 Hz half-sum, and low-frequency beats 5-14 Hz half-difference. The 78 Hz oscillation functions described above, while the low-frequency beats corresponded to a- and r-rhythms of the brain, which, also plays a key role in achieving the goal of increasing the effectiveness. As will be described below, the frequency of 78 Hz helps to increase the concentration of neurotransmitters such as beta-endorphins and serotonin in brain structures. Along with this, electromagnetic low-frequency beats also provide an additional increase in the concentration of these neurotransmitters.

Referring now to FIG. 1, there is a schematic showing the general components of a device 100 consistent with an embodiment of the present invention. Included are at least a control interface, digital isolator, microcontroller, pulse-width modulator, inversion operational amplifier, analog switch, voltage-controlled current source, and a power isolator. An extensive schematic of the device (and embodiments thereof) of the present application may be found in application 63/139,580 which is incorporated by reference herein.

Figure 2:
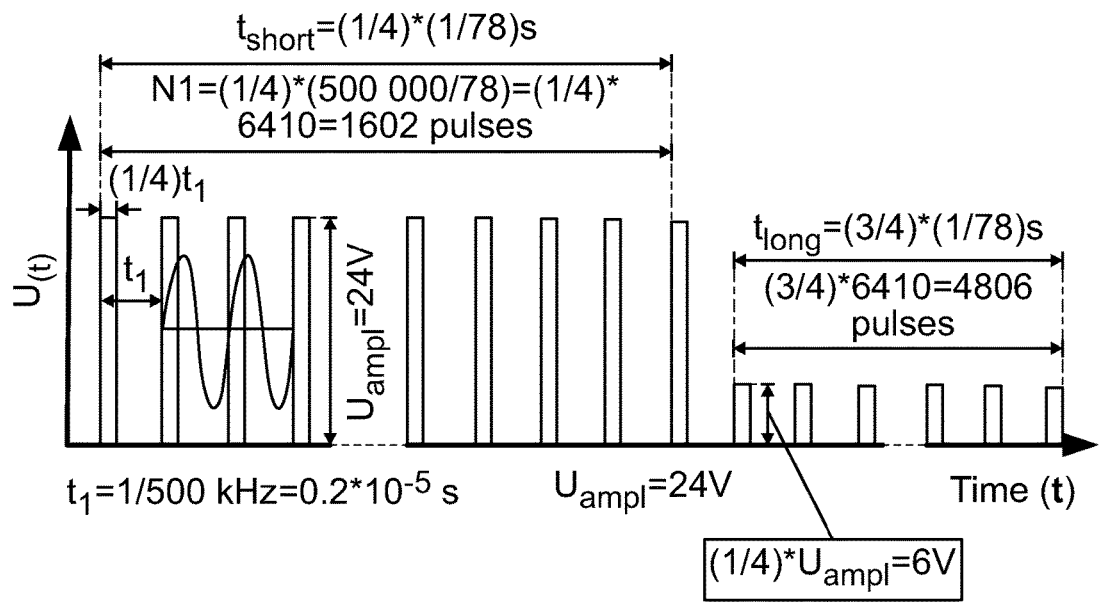
FIG. 2 is a diagram showing both a monopolar and bipolar carrier frequency being modulated by a modulating frequency.
Figure 2:
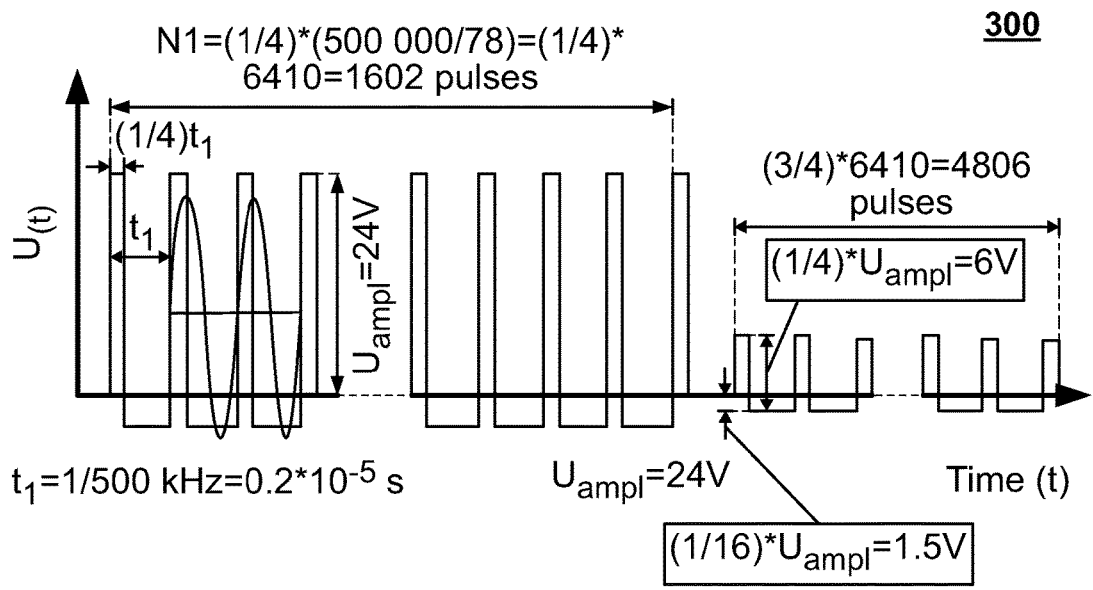

Referring now to FIG. 2, there is a diagram showing both a monopolar 200 and bipolar 300 carrier frequency being modulated by a modulating frequency. Each of the monopolar 200 and bipolar 300 diagrams are charted over time.

The low-frequency dielectric constant of the human brain is e=2860. The speed of an electromagnetic wave in the substance of the brain is calculated according to the equation $$V=C/n=C/(e)^{1/2}=(3.10^8)/(54)=6.10^6 \text{м}/c=6000 \text{ km/s}$$

The length of the electromagnetic wave in the substance of the brain is calculated according to the equation.

$$l=V/f=(6\,000\,000)/(5\,00\,000)=12 \text{ m}$$

Thus, the length of the electromagnetic wave in the substance of the brain is 12 m with a frequency of electromagnetic oscillations of 500 kHz. The arrangement of pairs of "forehead-to-head" and "temple-temple" electrodes is such that the distance between sources of electromagnetic waves emitted by the electrodes is small. This distance is much less than the length of the electromagnetic wave in the substance of the brain. From this, it follows that the electromagnetic oscillations of both sources occur in the same phase. That is, the phase difference of oscillations between them is zero. This means that both oscillations simultaneously reach a maximum, simultaneously pass through zero, and at the same time reach a minimum.

Therefore, the interference of waves propagated in the brain substance by emitters at 500 kHz, with zero phase difference, created a simple mutual increase in the amplitude of pulses. Without the distortion of the pulse shape and without changing of the frequency. Such pulsed oscillations with a frequency of 500 kHz can, of course, be decomposed into the Fourier spectrum with frequencies that are multiples of 500 kHz. But all Fourier components of different frequencies do not undergo distortion for the reason described above. Therefore, they are added to each other in the interference zone without phase shift. After the addition, in the interference zone, they create undistorted pulsed oscillations, doubling the amplitude of each Fourier component.

A fundamentally different situation exists for oscillations modulating the carrier frequency. Both radiators of modulating oscillations oscillate with different frequencies and propagate in the substance of the brain at different speeds. Therefore, between the modulating oscillations, there is initially a phase difference, the magnitude of which varies periodically in the interference zone. For this reason, in the interference zone occur carrier frequency oscillations (500 kHz), which are modulated in a complex manner. In this complex oscillation, there are two frequencies equal to the half-sum and half-difference of the modulating frequencies (44 Hz and 34 Hz). This is true for the main sine-wave Fourier harmonic of each modulating pulse oscillation. The view of the main harmonic is presented in FIG. 2. Higher Fourier harmonics do not play a significant role in the described process, since their amplitudes are small.

Figure 3:
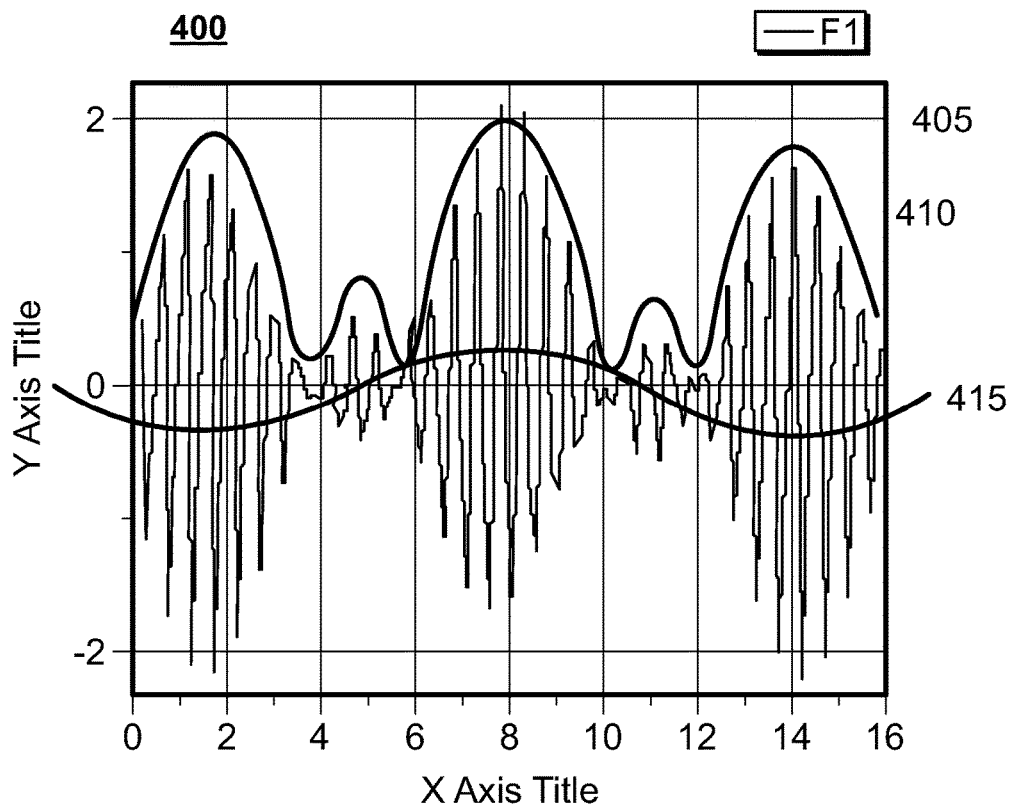
FIG. 3 is a diagram illustrating a resultant carrier frequency modulated in accordance with FIG. 2.
Figure 4:
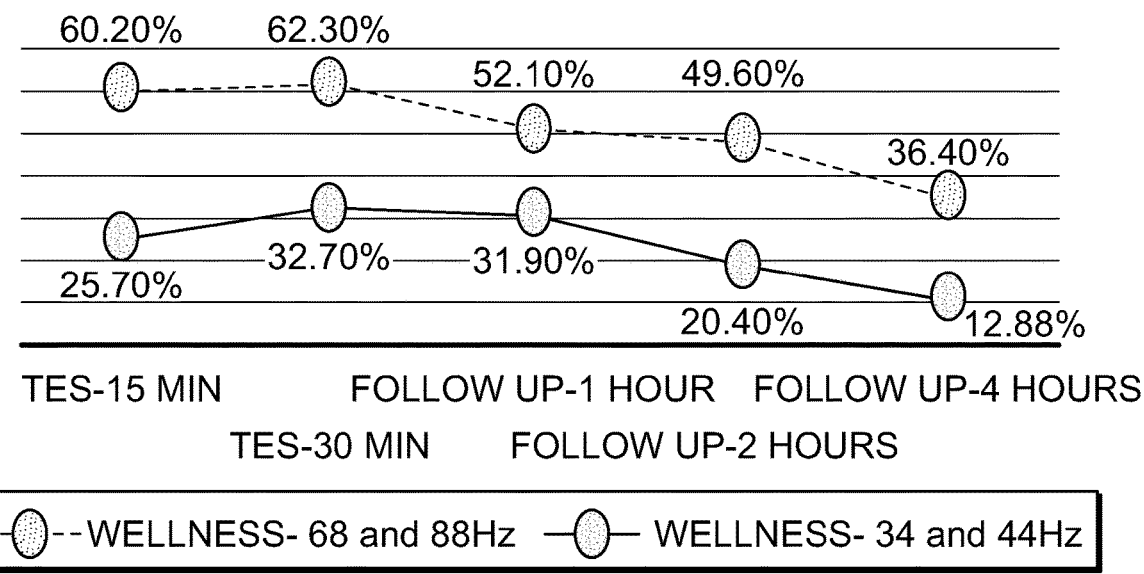
FIG. 4 is a chart illustrating the resulting of pain threshold tolerances of an animal in accordance with an application of an embodiment of the present application.
Figure 5:
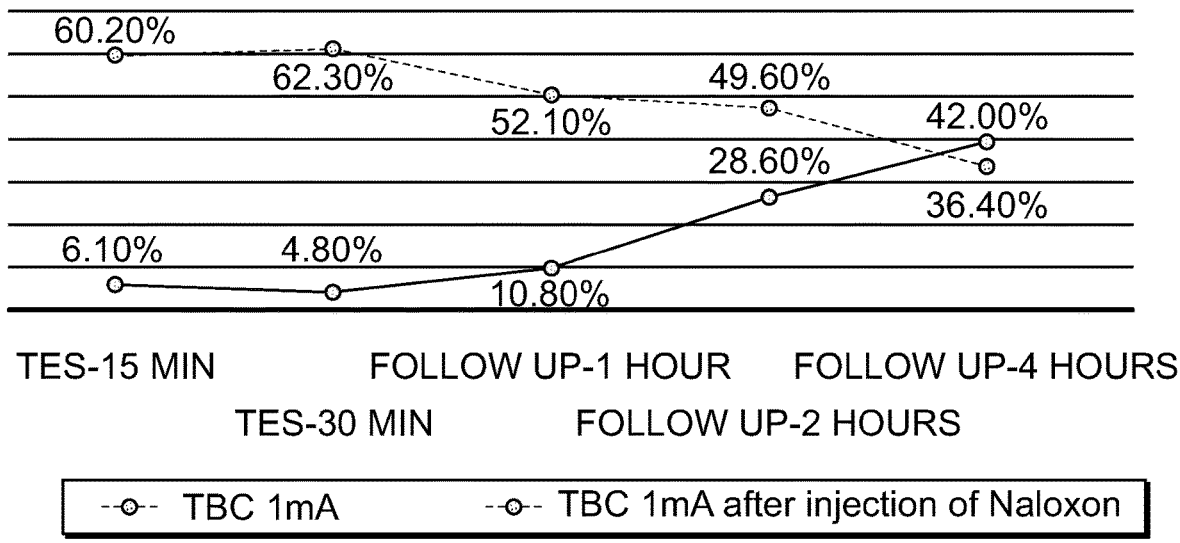
FIG. 5 is a chart illustrating the resulting of decreasing of pain threshold tolerances of an animal after injection of Naloxone in accordance with an application of an embodiment of the present application.
Figure 6:
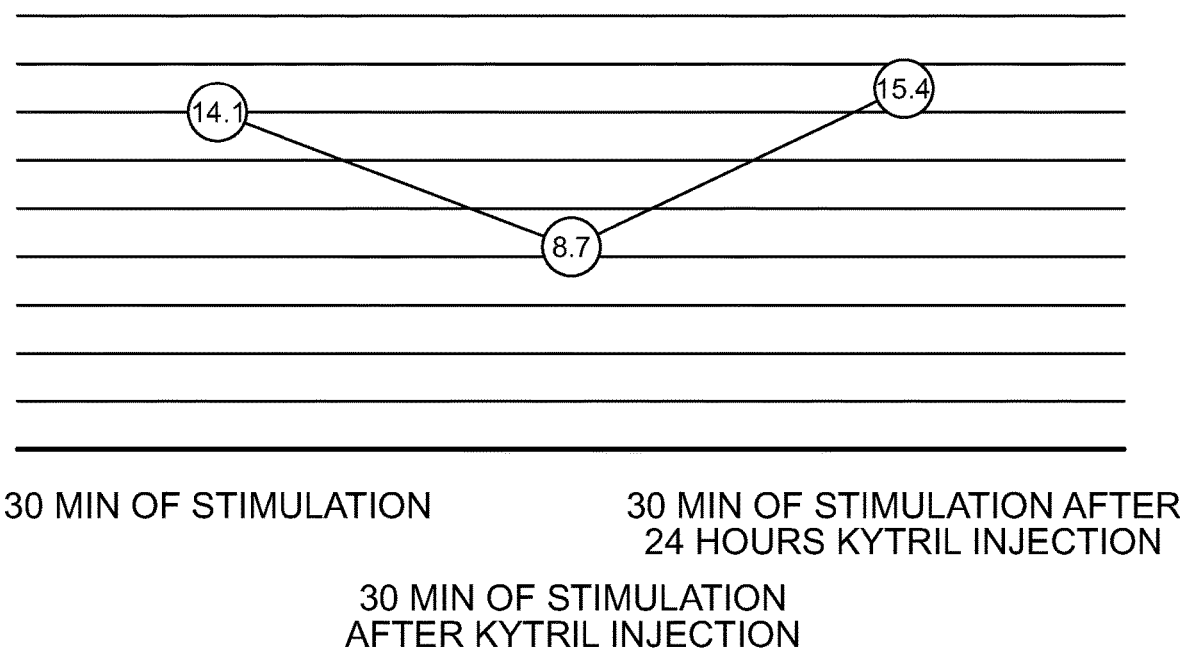
FIG. 6 is a chart illustrating the resulting of slowing down the development of a conditioned reflex of an animal and restoration of the development of conditional reflex after injection of Kytril (Granisetron) (antagonist of serotonergic receptors) in accordance with an application of an embodiment of the present application.

The resulting oscillation modulating the carrier frequency is shown in FIG. 3. This graph 400 clearly shows the high-frequency oscillation 405 of the carrier frequency, as well as two other oscillations with sharply differing frequencies. One frequency 410 is equal to the half-sum frequency of the main Fourier harmonics of the modulating oscillations. For 34 Hz and 44 Hz this gives a value of 39 Hz. The other frequency 415 is equal to the half-difference of these frequencies, and for 34 Hz and 44 Hz it is 5 Hz. It follows that to obtain 78 Hz and 10 Hz, a doubling of frequencies is required, modulating the carrier 500 kHz. That is, why we must use the modulating frequency of 68 Hz and 88 Hz. Based on the presented above theoretical hypothesis, a comparison was made of 34 and 44 Hz and 68 and 88 Hz, used to obtain modulating frequencies of 77 and 10 Hz. It was experimentally confirmed, as shown in FIG. 4 that the most pronounced effect manifested in an increase in the pain threshold, occurs when using a narrow range of frequency characteristics of 68 and 88 Hz. The use of 34 and 44 Hz caused a statistically significantly smaller increase in the pain threshold. It should be noted that an increase in the pain threshold was blocked as shown in FIG. 5 by the administration of a beta-endorphin antagonist—Naloxone. It was also experimentally confirmed, as shown in FIG. 6, that pronounced effect, manifested in slowed down the development of a conditioned response, which explained by the stimulation of serotonergic structures, was blocked as shown in FIG. 6 by the administration of the serotonin's receptors antagonist—Kytril (Granisetron).

EXAMPLE

1. The frequencies used to achieve the modulating frequencies by interference:

Bipolar pulses with a frequency:
Chanel #1: 88-96 Hz (+/−2.5%)
Chanel #2: 62-68 Hz (+/−2.5%)
Modulating frequencies occurring in the interference zones 76-80 Hz and 9-12 Hz.
2. Carrier frequency:
Bipolar pulses with a frequency of 300-500 kHz+/−10%, (random frequency changes every 120 seconds, step 20 kHz, +/−10%)
Polarity changes every 600 seconds.
Polarity reversal time 30 seconds (15 seconds of current decreases to zero, and 15 seconds of current is set to the value preceding the change in polarity)
The duration of the positive phase of the pulse is ¼ period
The duration of the negative phase of the pulse is ¼ period
Area of the positive phase=area of the negative phase
3. Frequencies used to achieve modulating frequencies:
Bipolar pulses with a frequency: 62-68 and 88-96 Hz, (+/−2.5%)
frequency changes randomly every 120 seconds, stage 2 Hz (+/−10%)
Polarity changes every 600 seconds.
Changes in the polarity of the modulating frequencies must be synchronized with changes in the polarity of the carrier frequencies.
The duration of the positive phase of the pulse is ¼ period
The duration of the negative phase of the pulse is ¾ period
Area of the positive phase=area of the negative phase
The modulation depth of the positive and negative phases of the pulse is 66.7%.
Area of the modulated positive phase of the pulse=area of the modulated negative phase of the pulse
4. The output is stabilized by current
5. Change the value of the amplitude of the current in the range 0-40 mA
6. The ratio of the amplitude of the current in the positive and negative phases of modulated and unmodulated pulses ⅓
7. The exposure time is a multiple of 10 minutes but does not exceed one hour.
8. Location of electrodes:
First pair: Forehead—Neck (Chanel #1)
Second pair: Temple—Temple (Chanel #2)
Third pair: Mastoid—Mastoid (Chanel #2)

In practice, a generator is configured to produce a 500 kHz frequency and two low-frequency carrier modulating oscillators with frequencies 88 Hz (supplying basal electrodes) and 68 Hz (supplying mastoid electrodes). Each pair of electrodes consists of two metal plates connected to one of the two channels. The block diagram also contains a control computer and a control monitor.

A high-frequency bipolar impulse with a repetition frequency of 500 kHz has a duty cycle of ¼ and an amplitude of 24 V or less for the short pulse and 8 V or less for the longer pulse. The length of an electromagnetic wave in a vacuum corresponding to the basic sinusoidal harmonic of a high-frequency carrier is $\lambda=c/v=3\cdot10^{8}/(5\cdot10^{5})=600$ m. In the medium shielding the electric field, i.e. in the brain, it is less by n times $-\lambda/n$, where $n=(\varepsilon)^{1/2}=50$, a $\varepsilon=2500$ is the low-frequency permittivity of brain tissue. Taking this into account, the wavelength is 12 m, i.e., much larger than the transverse dimensions of a head. As a consequence, the interference pattern appearing in the brain is a homogeneous, spatially limited area in which the oscillations are added and electrical pulsations, i.e. vibrations of electromagnetic fields and currents are performed.

It should be noted that the time dependence of the current density amplitude does not coincide with the time dependence of the amplitude of the applied bipolar voltage meander. The fact is that the head has an electrical resistance, which in the general case is complex. Calculation of the simplest equivalent circuit of the brain with superimposed electrodes by the complex method leads to the discovery of significant differences in the shape of current density oscillations and the applied voltage.

Such an equivalent circuit contains an electrical capacitance as well as two resistances, a charging and discharging one, simulating the conductivity of brain tissue. The capacitance is due to a pair of electrodes with a medium with a sufficiently high dielectric constant $\varepsilon=2500$ between them (dense brain tissue and basal cisterns filled with cerebrospinal fluid). The charge resistance simulates the contact resistance of the scalp and skull bones of the animal, the discharge resistance connected in parallel with the capacitance that simulates the ability of the brain tissue to shield the external field represents the electrical resistance of the internal brain tissue. The time constant $\tau$ of such a circuit is determined by the expression $\tau=(CR_{charge}R_{discharge})/(R_{charge}+R_{discharge})$ and is estimated by us to be 6 µs (C=100 pF, $R=5\cdot10^{4}\Omega$, $R_{discharge}=10^{5}\Omega$), which is much longer than the high-frequency voltage period $1/f=(\frac{1}{5})\cdot10^{5}$ s=$2\cdot10^{4}$ s. Said means that the short time pulses of impulse will be reintegrated in percent more effectively than the time extended pulses of opposite polarity, it means that during integration into RC-chain the initial equality of pulse areas of opposite polarity will change in favor of the time extended part of the bipolar pulse. In other words, the integral midline of the bipolar impulse will be significantly shifted towards its wide pulses, so that in addition to the alternating current component, a direct current will flow between the electrodes in one predominant direction.

It should also be taken into account that the addition of the electromagnetic field oscillations in the area of intersection of orthogonal current tubes will lead to the appearance of a series of flat Lissajous figures in this area, located in several layers parallel to the electrode plane. The appearance of these figures, which determine the direction of the total current vector and the electromagnetic field vector, is determined by the phase difference between the oscillations of the same-named Fourier-harmonics of the folded orthogonal currents and electromagnetic fields.

Modulation of the high-frequency voltage was conducted in our applied electric circuit by bipolar low-frequency impulses: 88 and 68 Hz. The modulating impulses had a duty cycle of 4 and performed a 75% modulation of the signal. As a result of modulation, mutually orthogonal currents of alternating polarity flowed in the brain along with unidirectional mutually orthogonal currents. The latter is the area where the current tubes crossed excited mainly low-frequency oscillation beats. The form of Lissajous figures and their changes in time are very difficult to analyze because of the multifactorial character of the processes going on: the presence of different modulation frequencies, complicated law of phase shift change in the time between different Fourier-harmonics generated by all the voltage sources, complex branching in the animal brain currents into separate "streams" and so on. Nevertheless, the analysis shows that the main frequencies of the low-frequency oscillations are the half-sum and half-difference frequencies of 68 and 88 Hz modulating the high-frequency carrier, namely 78 Hz and 5-14 Hz, a combination which represents the set of optimal frequencies for effective deep brain TES. The positive technical aspects of the implementation of the interference algorithm for animal brain TEC:

1) The use of two or more pairs of electrodes providing a summation process in a volume-limited area reduces the amount of total current flowing through the brain. The reason for this is the pumping of energy into the working zone from areas of the brain not captured by the interference zone, according to the principles of coherent interference summation;
2) Choosing the position of the electrodes on the surface of the skin allows the spatial arrangement of the limited volume area of intersecting mutually perpendicular current tubes inside the animal's head to be changed, allowing for greater research possibilities;
3) The use of two or more pairs of electrodes with modulation of 88 and 68 Hz allows the generation of 78 Hz frequencies and periodic current pulsations in the low-frequency range of 5-14 Hz, which are effective for TES;
4) Rapidly varying beats in the form of multidirectional Lissajous figures involve different micro-parts of the brain within the interference area, which reduces the "habituation" of brain tissues to TES. In early variants of TES implementation, habituation forced a continuous increase of the working voltage at the electrodes in order to compensate the decrease of TES efficiency as a result of the "compensatory" habituation mechanism; and
5) Changing the direction in space of current and field vectors (Lissajous figures) prevents electrical ionic polarization of the basal cistern cerebrospinal fluid. The polarization process made it necessary to change the polarity of the direct current every 15-20 min of the TES in order to avoid the "habituation" effect. The use of current interference also helps to reduce such a negative effect as an uncontrolled spontaneous increase in the amplitude of bipolar impulses during the first 5-10 min of TES, with their decrease during the next 5-10 min.

TES gives pronounced results when using pulsed electric current exposure as opposed to using sinusoidal exposure. The fact is that an external electrical pulse, when applied to a biological system, triggers a cascade of electrochemical reactions, each of which is characterized by its own relaxation time. Thus, the action potential of a neuron consists of several phases and lasts several milliseconds, with the first phase, the beginning of which is determined by the triggering threshold, having a duration of less than 1 millisecond.

Thus, the present data have established that activation of serotonin and endorphins production in the brain structures is caused not only by TES—activation of serotonergic and endorphinergic brain structures by TES at 78 Hz frequency while effective, but it could also be utilized connected with resonance amplification of α- and θ-brain waves, capable of causing cause a neuromodulatory effect. This is made possible by the occurrence of Fourier harmonics at 10 and 5 Hz using the interference pulse algorithm of the TES. An increase in a-wave amplitude caused by resonance activation causes an increase in beta-endorphin concentration, resulting in a reduction of stressors on the body, in particular those related to pain. This methodology could increase the level of response while simultaneously lowering the amperage and stabilizing neuro-homeostasis.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A method of increasing pain threshold via a wellness device, the method comprising the steps of:
    applying, to a user, a first set of bipolar pulses having a first frequency,
        wherein the first frequency is in a range of about 88 Hz to about 96 Hz;
    applying, to the user, a second set of bipolar pulses having a second frequency,
        wherein the second frequency is in a range of about 62 Hz to about 68 Hz;
    applying, to the user, a carrier frequency,
        wherein the carrier frequency is in a range of about 300 kHz to about 500 kHz;
    wherein the first set of bipolar pulses and the second set of bipolar pulses and the carrier frequency are applied to the user via electrodes; and
    wherein the first set of bipolar pulses and the second set of bipolar pulses create interference at about 9 Hz to about 12 Hz and/or 76 Hz to about 80 Hz.

2. The method of claim 1 wherein the carrier frequency is monopolar.

3. The method of claim 1 wherein the carrier frequency is bipolar.

4. The method of claim 1 further comprising the step of:
    applying, to a user, a modulating frequency in a range of about 9 Hz to about 12 Hz and/or about 76 Hz to about 80 Hz.

5. The method of claim 1 wherein a polarity of the carrier frequency is periodically inverted after a set time.

6. A method of increasing pain threshold via a wellness device, the method comprising the steps of:
    applying, to a user, a first set of bipolar pulses having a first frequency,
        wherein the first frequency is in a range of about 88 Hz to about 96 Hz;
    applying, to the user, a second set of bipolar pulses having a second frequency,
        wherein the second frequency is in a range of about 62 Hz to about 68 Hz;
    applying, to the user, a carrier frequency,
        wherein the carrier frequency is in a range of about 300 kHz to about 500 kHz,
        and
        wherein a polarity of the carrier frequency is periodically inverted;
    wherein the first set of bipolar pulses and the second set of bipolar pulses and the carrier frequency are applied to the user via electrodes; and
    wherein the first frequency and the second frequency create interference at about 9 Hz to about 12 Hz and/or 76 Hz to about 80 Hz.

7. The method of claim 6 wherein a ratio of a duration of a negative polarity of the carrier frequency to a positive polarity of the carrier frequency is about 3:1.

8. The method of claim 6 wherein the electrodes are coupled to a forehead, a temple, and a mastoid of a user.

9. The method of claim 8 wherein there are a pair of electrodes located at each of the forehead, the temple, and the mastoid of the user.

10. The method of claim 6 wherein a polarity of the carrier frequency changes about every 600 seconds.

11. The method of claim 6 wherein a frequency of the first frequency and the second frequency changes about every 120 seconds.

12. The method of claim 11 wherein a change in the first frequency and the second frequency is synchronized with a change in polarity of the carrier frequency.

13. The method of claim 6 wherein the bipolar pulses are applied for no longer than 60 minutes.

14. The method of claim 6 wherein an area under a positive phase of the first bipolar pulse and the second bipolar pulse is equal to an area under a positive phase of the first bipolar pulse and the second bipolar pulse.

15. The method of claim 6 wherein a modulation depth of a positive phase and negative phase of the first bipolar pulse and the second bipolar pulse is about 66.7%.

16. A method of stimulating serotonergic structures, experimentally confirmed by a slowdown in the development of a conditioned reflex via a wellness device, the method comprising the steps of:
- applying, to a user, a first set of bipolar pulses having a first frequency;
- applying, to the user, a second of bipolar pulses having a second frequency,
  - wherein the first frequency is greater in value than the second frequency;
- applying, to the user, a carrier frequency;
- wherein the carrier frequency is in a range of about 300 kHz to about 500 kHz;
- wherein the first set of bipolar pulses and the second set of bipolar pulses and the carrier frequency are applied to the user via electrodes; and
- wherein the first set of bipolar pulses and the second set of bipolar pulses create interference at about 9 Hz to about 12 Hz and/or 76 Hz to about 80 Hz.

* * * * *